Figure 1:
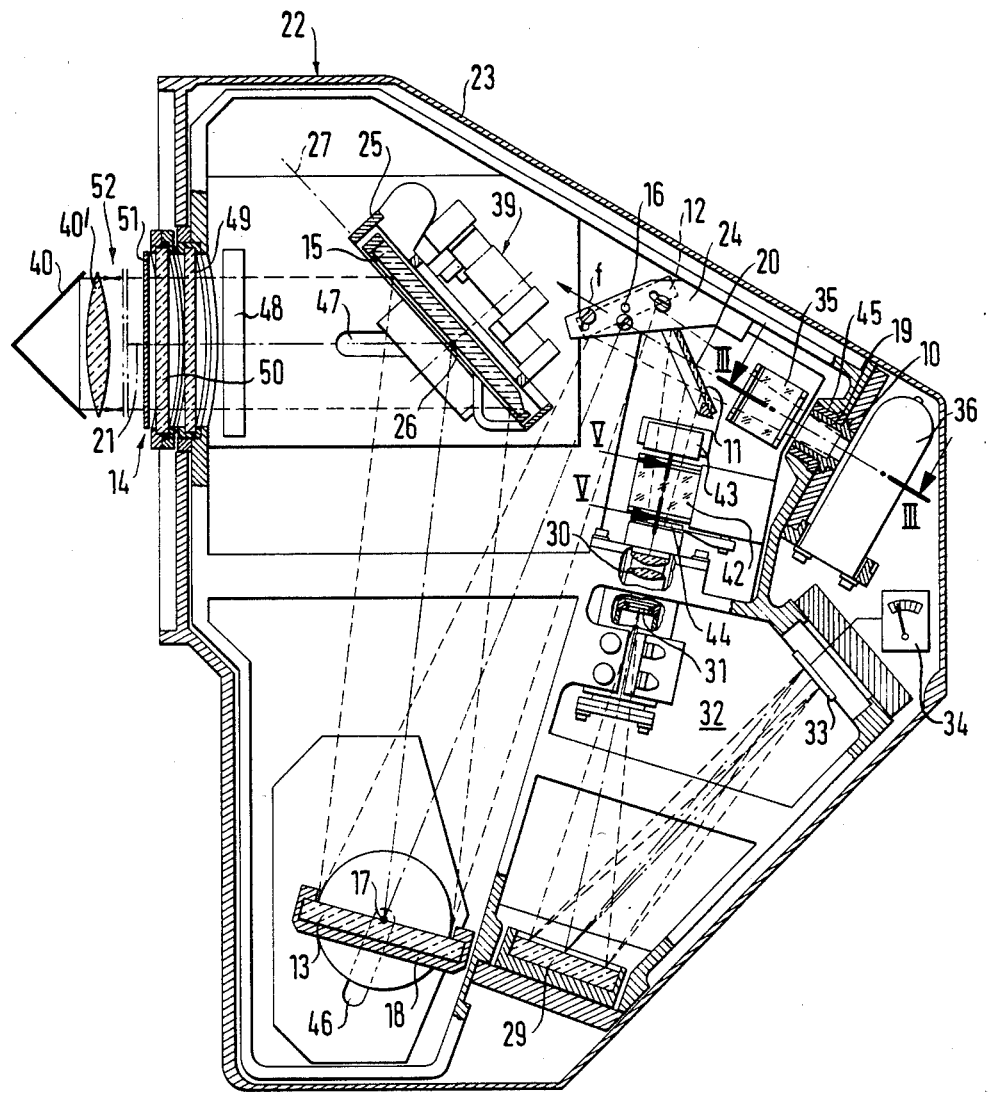

United States Patent [19]

Fetzer et al.

[11] Patent Number: 4,794,258
[45] Date of Patent: Dec. 27, 1988

[54] SPECTROANALYTICAL GAS MEASURING APPARATUS

[75] Inventors: Günter Fetzer, Gundelfingen; Jürgen Kaufmann, Denzlingen; Hans-Jürgen Schneider, Emmendingen; Frank Strohbusch, Denzlingen, all of Fed. Rep. of Germany

[73] Assignee: Erwin Sick GmbH Optik-Elektronik, Waldkirch, Fed. Rep. of Germany

[21] Appl. No.: 65,996

[22] Filed: Jun. 24, 1987

[30] Foreign Application Priority Data

Jul. 21, 1986 [DE] Fed. Rep. of Germany ....... 3624567

[51] Int. Cl.$^4$ ............................................. G01N 21/35
[52] U.S. Cl. ....................................... 250/373; 250/343; 250/347; 250/504 R; 356/437
[58] Field of Search ............... 250/373, 372, 343, 348, 250/347, 504 R; 356/305, 334, 328, 439, 438, 437

[56] References Cited

U.S. PATENT DOCUMENTS

| | | | |
|---|---|---|---|
| 3,816,741 | 6/1974 | Macall | 250/347 |
| 4,126,396 | 11/1978 | Hartmann et al. | 356/434 |
| 4,268,170 | 5/1981 | Flint | 356/334 |

FOREIGN PATENT DOCUMENTS 2023369 12/1979 United Kingdom ............... 250/347

*Primary Examiner*—Janice A. Howell
*Assistant Examiner*—Constantine Hannaher
*Attorney, Agent, or Firm*—Townsend & Townsend

[57] ABSTRACT

A spectroanalytical gas measuring apparatus has a radiation source (36), a transmitting condensor (19), an objective (13) and a beam divider (11) which deflects at least a part of the radiation reflected back to the apparatus by a reflector (40) to a polychromator or spectrometer (32). The transmitted radiation falls after the beam divider (11) onto a deflecting mirror (12) which is adjustable between two positions and which directs the light to an objective reflector (13). The objective reflector (13) reflects the radiation to a follow-up mirror (15) arranged opposite to the beam passage opening (14). At least one long and one short focal length objective reflector (13) are provided in order to ensure different ranges of distance in conjunction with the adjustable deflecting mirror (12).

33 Claims, 3 Drawing Sheets

SPECTROANALYTICAL GAS MEASURING APPARATUS

The invention relates to a spectroanalytical gas measuring apparatus comprising a source of electromagnetic radiation the spectrum of which transmits at least the spectral regions required for the gases to be determined; a transmitting condensor positioned after the source; an objective lens which forms an image of the condensor through a beam passage opening in the housing of the apparatus at a reflector provided at the end of the measurement path; and a beam divider arranged between the condensor and the objective lens for deflecting at least a part of the light reflected back on itself by the reflector to a polychromator (spectrometer), which splits the spectrum up into its components and directs it to a photoreceiver arrangement which delivers electrical signals respectively associated with specific wavelengths or with a specific narrow range of wavelength; wherein said signals are applied to an electronic processing circuit which effects a determination of the presence and/or quantity of the gases to be determined in dependence on the electrical signals received.

Spectroanalytical gas measuring apparatus of this kind is for example provided on waste gas chimneys in order to determine the quantity of noxious gases contained in the exhaust gas, in particular $SO_2$ and NO, so as to make it possible to control the combustion process or furnace to produce as few noxious substances as possible. The radiation which is used for this purpose lies in the ultraviolet range of wavelengths and preferably includes the spectral range lying between 200 nm and 320 nm.

It is however a problem that a gas measuring apparatus of this kind is generally only suitable for a quite specific range of distances so that it is only suitable for use with ranges of measurement paths of restricted lengths.

The object of the invention is now to provide a gas measuring apparatus of the initially named kind which, while having a compact construction, being simple to manufacture and also satisfying the highest optical accuracy, can be adjusted without problem to at least two different ranges of distance.

In order to satisfy this object the invention provides that the beam impinges after the beam divider onto a deflecting mirror which is adjustable substantially in the beam impingement direction between two positions and which deflects the beam to an objective reflector, said objective reflector being preferably formed as a concave mirror which directs the beam to a follow-up mirror which in turn deflects the incident light to the beam passage opening; that the deflecting mirror is displaceable between a first position in which the beam passes in front of the follow-up mirror and a second position in which the beam passes behind the follow-up mirror, and is also tiltable about a tilt axis perpendicular to a plane defined by the incident and emergent beams in such a way that radiation is in each case deflectable to the objective reflector; and that a longer focal length and a shorter focal length objective are interchangeably provided which are arranged on a holder tiltable about an adjustment axis arranged parallel to the said tilt axis and displaceable substantially in the direction of the incident radiation.

The objective reflector is expediently made exchangeable with this arrangement so that objective reflectors with different focal lengths can be used in each position, and in particular in different positions of the deflecting mirror. When the deflecting mirror is located in the position close to the condensor a short focal length objective reflector is used while a longer focal length objective reflector is used when the deflecting mirror is in the position remote from the condensor.

In this way it is for example possible, with two short focal length objective reflectors with focal lengths of 31 and 40 cm reflectively, and with the deflecting mirror located in the position close to the condensor, to cover ranges between 0.85 and 4.90 m whereas, on building in for example two long focal length objective reflectors with a focal length of 50 and 61 cm respectively, and with the deflecting mirror located in the position remote from the condensor, a further range of distances from 4.5 m to 13 m can be covered with the beam diameter being 6 cm in the first case and 7 cm in the second case.

It is particularly important that the same optical components are used for both ranges of distance apart from the objective that is exchanged, with only the mechanical arrangement having to be changed in the sense of the invention.

The combination of an autocollimation radiation transmitter-receiver apparatus with a polychromator in the receiver part represents an important basic concept of the invention. It is important that a dispersion free image forming element in the form of the objective reflector is used in the transmitted beam path because in this way falsification of the spectral measurements by the optical system can be largely avoided. The use of an objective reflector constructed as a concave mirror also has optical advantages in addition to the compact overall construction.

A constructionally particularly favourable arrangement is characterised in that the beam divider is arranged substantially at the level of the beam passage opening, and in that the deflecting mirror is located in the first position directly behind the beam dividing mirror.

For the same purpose provision is preferably made that the beam of radiation extending from the transmitting condensor to the beam divider and the deflecting mirror subtends an angle of 20 to 40° and in particular of approximately 30° to the emergent radiation beam.

In this arrangement it is expedient for the side of the housing in the region of the deflecting mirror to likewise subtend the angle of 20 to 40° and in particular of approximately 30° to the emergent radiation beam.

For a constructionally compact arrangement which requires little space it is furthermore useful for the deflecting mirror to be arranged in the first position at substantially the level of the follow-up mirror and preferably slightly higher than the latter.

It is furthermore expedient for this purpose for the deflecting mirror to be arranged in the second position higher than the follow-up mirror and between the follow-up mirror and the beam passage opening.

An arrangement which is favourable to manufacture, and which can also be simply adjusted by untrained persons, is characterised in that the deflecting mirror is pivotably arranged about the tilt axis in a holder which can be fixed in two positions on the housing.

An advantageous further development of the invention is characterised in that the objective reflector and its holder are arranged beneath the follow-up mirror in such a way that the angle of reflection at the objective reflector is as small as possible, and preferably amounts to 5 to 7°.

The follow-up mirror is expediently mounted in an outer holding device which is preferably mounted on the housing so as it is displaceable in the direction of the beam passage opening.

It is particularly advantageous for an additional adjustment possibility for the follow-up mirror to be provided by arranging for the follow-up mirror in the outer holding device to be pivotable about two positioning axes which are perpendicular to one another, preferably by a control motor arrangement. In this way the gas measuring apparatus of the invention can be aligned without problem with a reflector provided at the end of the measurement path, with this reflector generally being constructed as a retroreflector.

The retroreflector is preferably a single triple mirror, expediently with a lens arranged in front of it, with the focal length of the lens being the same as half the distance between the beam passage opening and the reflector.

In order to ensure a problemfree possibility of adjustment for the follow-up mirror, provision should in particular be made for the one positioning axis to extend parallel to the said tilt axis and for the other positioning axis to extend perpendicular to the first positioning axis and parallel to the surface of the follow-up mirror.

Furthermore, it is useful for the holding device to be fixable in the housing in two positions which are rotated through 180° relative to one another about the vertical axis. This ensures that in the one position the space behind the follow-up mirror and in the other position the space over the follow-up mirror can be ideally exploited for the light beam.

In the sense of compactly accommodating also the polychromator, the invention further provides that the beam divider reflects the bundled received beam to the polychromator substantially parallel to the transmitted radiation beam reflected by the deflecting mirror in the first position.

With this arrangement provision should in particular be made for the beam divider to reflect the received radiation to a receiving condensor which forms an image of the objective reflector on the entry gap of the polychromator.

In order that all the light beams which are used for the main measurement are located in one plane it is furthermore expedient for the grating of the polychromator to diffract the received radiation into the same plane as that in which all the other beams of radiation extend, and for several photoreceivers which form the photoreceiving arrangement to be arranged at the angles of diffraction substantially at the spacing from the grating as the entry gap.

In order to achieve automatic concentration of the emergent radiation beams onto the reflector provision is made, in accordance with a further useful development of the invention, that an inclined, demirrored, beam divider plate, in particular a quartz glass plate, is located in the received radiation in front of the follow-up mirror, preferably between the beam divider and the transmitting condensor, and deflects the received beam preferably perpendicular to the plane of the radiation beam to a four-quadrant photoelement, which steers the follow-up mirror via a control circuit in such a way that the emergent radiation beam falls centrally onto the reflector.

In order to also be able to detect the dust content along the measurement path a further embodiment provides that an inclined beam deflecting plate which is demirrored for the radiation to be transmitted, in particular ultraviolet light, but which reflects visible light, in particular a quartz glass plate, is provided in the received radiation after the beam divider, preferably in front of the receiving condensor, and deflects the visible part of the received radiation outwardly, preferably perpendicular to the plane of the main radiation beam to a semiconductor detector which is sensitive to visible light and which serves for dust content measurement.

Finally, it is advantageous for calibration purposes when a reference cell containing a measurement gas can be swung into the received radiation beam after the beam divider.

Particularly simple installation and servicing and also repair is ensured when the radiation source which is preferably constructed as a deuterium lamp is built together with the transmitting condensor into a preadjusted constructional unit.

In order to achieve a light intensity which is as high as possible for the measurement, but nevertheless to protect the radiation source which is used, a particularly advantageous embodiment of the invention is characterised in that the radiation source which is preferably formed as a deuterium lamp is energised by a low basic DC current which lies substantially below the loading limit, but which however permits permanent operation, on which individual DC pulses are superimposed at specific time intervals which overload the radiation source for a short period of time.

The invention is thus also further based on the concept of overloading the lamp that is used for a short period of time and of carrying out a measurement of the spectral composition along the measurement path during this time, while the radiation source that is used is only energised with a minimal basic current between the rectangular pulse-like overloaded intervals which is just sufficient to keep it burning.

While the said measurement with individual rectangular DC pulses is necessary for the detection of the ultraviolet spectral range, the invention also makes provision, for carrying out dust measurements in the visible part of the spectrum, for pulse trains to be superimposed on the basic DC current in periods lying between said specific time intervals.

In this manner the invention takes account of the fact that a deuterium lamp cannot be energised with AC current. Since pulse trains consisting of individual pulses can be superimposed on the low basic DC current it is however possible with a deuterium lamp to generate AC light, such as is expediently used for dust measurement, in order to preclude the affects of background light.

Figure 2:
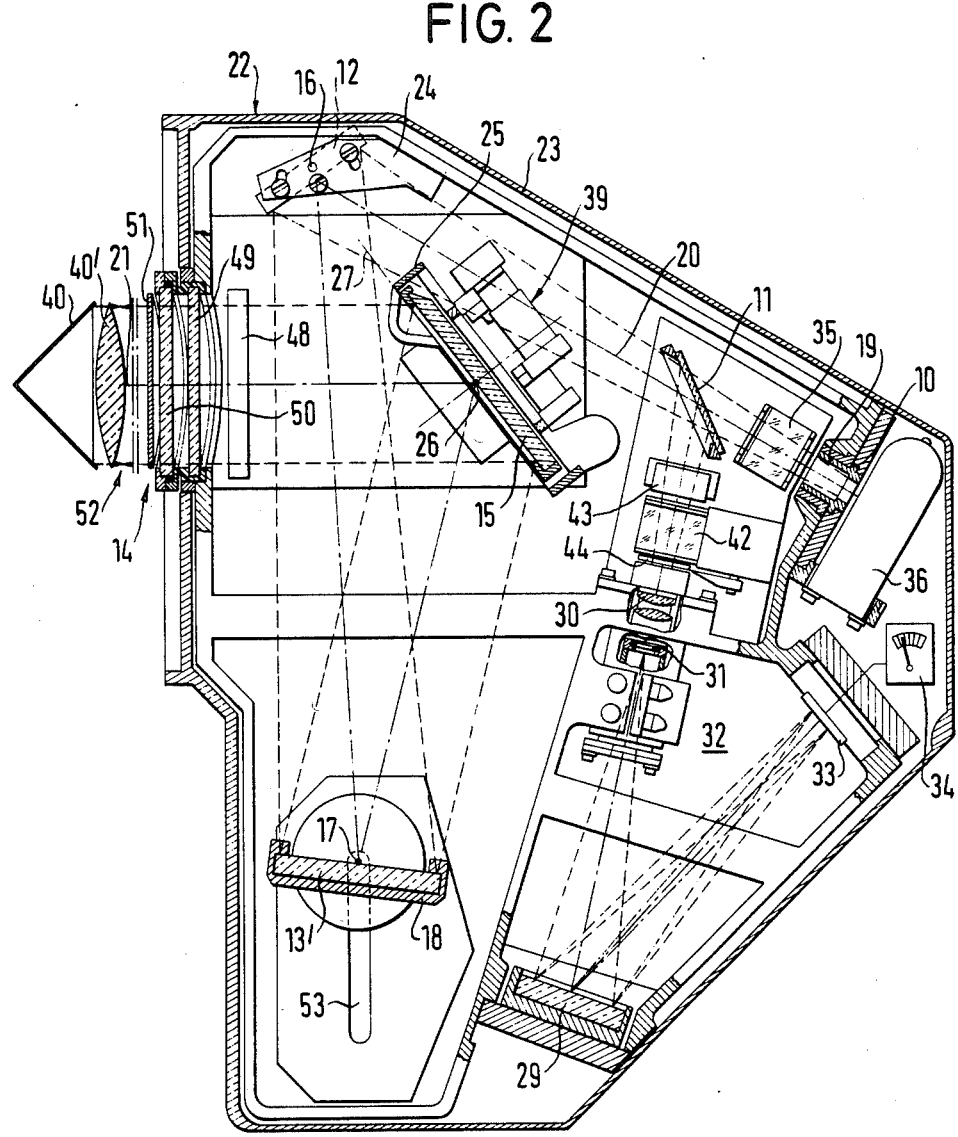
Figure 5:
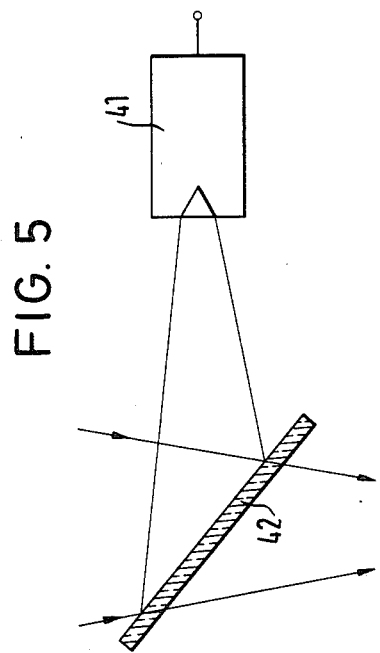
Figure 3:
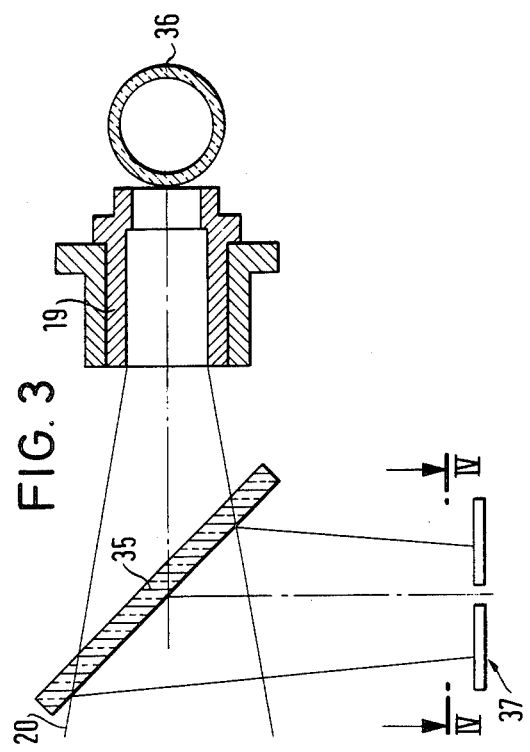
Figure 4:
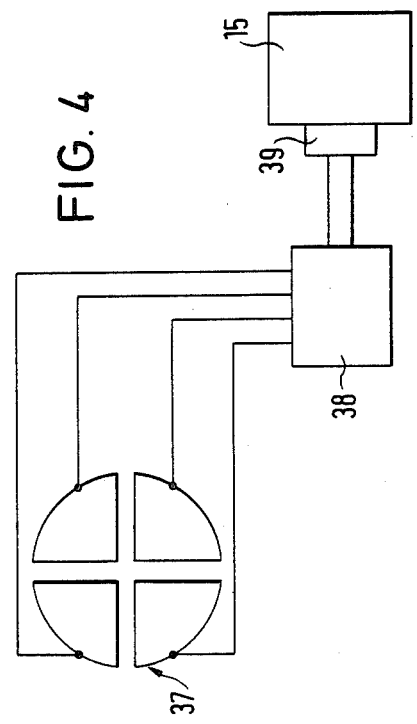

The invention will now be described in further detail by way of example and with reference to the drawings in which are shown:

FIG. 1 a partly schematic vertical section of a gas measurement apparatus in accordance with the invention along the optical axes of the light beams used for the main measurement, with the individual optical elements being located in the positions for a range of 0.85 to 4.90 m, FIG. 2 a section analogous to that of FIG. 1 of the same gas measuring apparatus however with the individual optical elements being disposed and fixed for a range of 4.5 to 13 m, FIG. 3 a somewhat enlarged section on the line III—III of FIG. 1, FIG. 4 a schematic view on the line IV—IV of FIG. 3 with further additional components being shown, and FIG. 5 a somewhat enlarged section on the line V—V of FIG. 1.

As seen in FIG. 1 a deuterium lamp 36 which is inclined at approximately 30° to the vertical is connected to a transmitting condensor lens 19 arranged in front of it to form a preadjusted unit 10 which can be exchanged without subsequent adjustment.

The deuterium lamp 36 which serves as the radiation source is energised with a stabilised DC basic current of approximately 120 to 180 mA on which rectangular DC pulses of 0.8 to 2 A and of 0.3 sec length are superimposed at intervals of for example 3 sec. The spectral measurement takes place in the ultraviolet range during these DC pulses.

Pulse trains with for example 10 pulses and a frequency of approximately 10 kHz are periodically superimposed on the bsic DC current between two DC rectangular pulses, i.e. between pairs of DC rectangular pulses. In this way light pulses arise which are used for the later described dust measurement.

An inclined, demirrored quartz glass plate 35 is arranged in the transmitted beam of radiation 20 after the transmitting condensor 19 and deflects a part of the received radiation perpendicular to the plane of the drawing of FIGS. 1 and 2 in the manner which will later be explained with reference to FIGS. 3 and 4.

The quartz glass plate 35 which also transmits ultraviolet light is followed by a spectrally neutral beam divider 11. The part of the transmitted beam of radiation 20 transmitted by the beam divider 11 passes to a deflecting mirror 12 which is restrictedly pivotable about a tilt axis 16 perpendicular to the plane of FIGS. 1 and 2 through an angle of 10 to 20°, and can be fixedly arranged in the adjusted position. On average the deflecting mirror 12 is tilted as approximately 45° to the direction of light incidence f.

The holder 24 is releasably secured to the inclined upper side of the housing 22 at the inside and can, apart from the position shown in FIG. 1 in the lower region of the upper side 23, also be fix in the upper region of the side 23 in accordance with FIG. 2.

The deflecting mirror 12 reflects the received transmitted light to an objective reflector 13 arranged in the lower region of the housing 22, with the objective reflector 13 expediently being in particular a spherical concave mirror with a focal length of 31.5 cm.

The objective reflector 13 is arranged in a holder 18 and is adjustable with the latter about an adjustment axis 17 standing perpendicular to the plane of FIGS. 1 and 2. An elongate slot 46 extending in the direction of the received radiation also makes it possible to change the distance of the objective reflector 13 from the deflecting mirror 12 within certain limits.

The objective reflector 13 reflects the radiation received from the deflecting mirror 12 approximately vertically to the follow-up mirror 15 which is arranged above it at approximately 45° to the horizontal and which is arranged in a holding device 25. The holding device 25 is displaceable in the direction of a radiation passage opening 14 of the housing 22 and located at the same height by means of its arrangement in a substantially horizontal elongate slot 46 and is tiltable about a positioning axis 26 which stands perpendicular to the plane of FIGS. 1 and 2.

After the adjustment to the desired range of distances the holding device 25 is fixed relative to the housing 22.

The follow-up mirror 15 is however arranged within the holding device 25 for restricted adjustment about two positioning axes 26, 27 which are perpendicular to one another, with the adjustment about the two positioning axes 26, 27 being capable of being effected by a control motor arrangement 39.

A zero point reflector 48, a window 49, a disk 50 which can be moved in and moved out, and an optical head stop 51 are arranged behind one another in the beam passage opening 14, or at the beam passage opening.

After the emergent radiation beam 21 has emerged through the beam passage opening 14 it extends along the measurement path 52 which can for example be formed by the interior of a chimney.

At the end of the measurement path 52 there is located a retroreflector 40 which reflects the incident light beams back on themselves to the light passage opening 14. In the illustrated embodiment the retroreflector 40 consists of a single triple mirror in front of which there is positioned a lens 40' having a focal length which corresponds to twice the distance of the retroreflector 40 from the beam passage opening 14. The lens 40' forms an image of the beam passage opening 14 on itself with a scale 1:1. In this manner an autocollimation beam path is formed, i.e. the radiation reflected from the retroreflector 40 can once again extend along the measurement path 52, and along the same path as that which the transmitted radiation takes, back to the beam divider 11, from which it is reflected substantially downwardly to the polychromator (spectrometer) 32.

Directly adjoining the beam divider 11 is a reference cell 43 which can be swung in and swung out after the received light has been deflected, and this is followed by a dichroic inclined quartz glass plate 42 which is demirrored for ultraviolet light, but which reflects visible light and which deflects the visible part of the received radiation perpendicular to the plane of FIGS. 1 and 2 in the manner which will later be described with reference to FIG. 5.

The quartz glass plate 42 is followed by a pivotable aperture diaphragm 44 and the receiving condensor 30 follows this in the beam path of the received light. It is also possible for the pivotable aperture diaphragm to be arranged at another suitable position, for example between the transmitting condensor 19 and the quartz plate 35.

The diaphragm for the deuterium lamp 36 is imaged by the transmitting condensor 19 in enlarged form into the objective reflector 13.

The objective reflector 13 is furthermore so arranged that it images the transmitting condensor 19 in enlarged form into the reflector 40. The receiving condensor 30 images the objective reflector 13 into the inlet gap 31 of the polychromator 32. From the inlet gap 31 the received radiation passes to the grating 29 of the polychromator 32 which is arranged beneath it, approximately at the level of the objective reflector 13, from where the received radiation is diffracted, ordered in accordance with its wavelengths, to a photoreceiver arrangement 33 which consists of a row of photoreceivers 33' arranged in a row one after the other. The photoreceivers 33' lie in one plane with the other components, namely in the plane of the drawing of FIGS. 1 and 2, and extend in the direction of different angles of diffraction of the received light.

As a result of the construction of the invention the photoreceiver arrangement 33 lies just below the lamp 36 while the polychromator 32 is accommodated as a whole in the triangular space defined by the lamp 36, the follow-up mirror 15 and the objective reflector 13, with the grating 29 being located approximately at the level of the objective reflector 13.

As seen in FIGS. 3 and 4 the part of the received beam which passes through the beam divider 11 in the direction of the transmitting condensor 19 is deflected by the obliquely arranged quartz glass plate 35 to a four-quadrant photoelement 37 which is connected to a control circuit 38 which controls the control motor arrangement 39 for the follow-up mirror 15 in such a way that the emergent light beam 21 is always concentrated on the retroreflector 40 through appropriate tilting of the follow-up mirror 15 about the positioning axes 26, 27. Optically the four-quadrant photoelement 37 is located at the same position as the transmitting condensor lens 19, so that the retroreflector 40 is imaged by the objective reflector 13 onto the four-quadrant photoelement 37.

As seen in FIG. 5 the further quartz glass plate 42 reflects a part of the received light to a semiconductor detector 41 which should be provided with a green filter in accordance with the sensitivity of the eye, so that a signal representative of the dust content of the exhaust gases on the measuring path 52 is transmitted at its electrical output.

The manner of operation of the described gas measuring apparatus is as follows:

The apparatus operates in accordance with the autocollimation principle, i.e. the beam path shown in FIGS. 1 and 2 applies to both the transmitted light and to the received light.

In FIG. 1 the deflecting mirror 12 is shown in its first position in which it reflects the light in front of the follow-up mirror 15 obliquely downwardly to the objective reflector 13, which in this case has a focal length of 31.5 cm. The objective reflector 13 makes the light coming from the lamp 36 and the transmitting condensor 19 parallel and guides it via the follow-up mirror 15 through beam passage opening 14 to the retroreflector 40. The received radiation follow the same path, is however deflected by the beam divider 11 to the polychromator 32.

The part of the received radiation incident on the four-quadrant photoelement of FIGS. 3 and 4 ensures automatic alignment of the follow-up mirror 15 onto the retroreflector 40.

In this manner a range of 0.85 m to 1.4 m is made possible with the described gas measuring apparatus with a beam diameter of 6 cm. With another objective reflector 13 of 40 cm one can cover a further range of distances of 1.4 to 4.9 m.

Should ranges of 4.5 to 13 m be detected with a beam diameter of 7 cm then, in accordance with FIG. 2, the deflecting mirror 12 must be displaced into its second position at the upper end of the housing 22 and fixed there. Furthermore the deflecting mirror 12 must be tilted about the axis 16 in the counter-clockwise sense so that the transmitted light which it receives passes to the objective reflector 13' which has a larger focal length of 50 or 61 cm for the detection of the larger and further removed range of distances. It is the only optical component which needs to be exchanged on changing the range of distances.

As seen in FIG. 2 the objective reflector 13' on its holder 18 is not only displaceable within the elongate slot 46 as seen in FIG. 1 but is also substantially vertically displaceable in the direction of a further elongate slot 53 which, in view of the larger focal length of the objective reflector 13', is substantially longer than the inclined elongate slot 46.

Moreover, the objective reflector 13' having the longer focal length must be so tilted about the adjustment axle 17 which stands perpendicular to the plane of the drawing that the reflected beam falls on the follow-up mirror 15 and is directed by the latter substantially horizontally through the light passage opening 14.

Thus two objective reflectors 13, 13' of different focal lengths are necessary for the different range of distances. In other respects it is only the deflecting mirror, the objective reflector and the follow-up mirror 15 which need to be adjusted when converting the apparatus from one range of distances to the other in the manner proposed by the invention.

The control motor arrangement 39 consists of two motors controlled by the control circuit 38 with incremental transducers and also position sensors which make it possible to correct the mirror position and also to move the mirror to a reference point after switching off the apparatus and in the control cycle.

The spectrum of the measurement gas contained in the reference cell 43 serves for checking the photoreceiver arrangement 33. The polychromator 32 can be covered over after the measurement by means of the pivotal aperture stop 44 and the dark current of the individual receivers of the photoreceiver arrangement 33 can be measured.

The zero point reflector 48 and the optical head diaphragm 51 serve for the self-monitoring of the apparatus in known manner. During the control cycle the zero point reflector 43 is pivoted into the beam path and the follow up mirror 15 is moved to the reference point, with the lamp power being subjected to follow-up control to the desired value with the aid of the received signal. The determination of the boundary surface contamination takes place by periodically moving the disk 50 into and out of the beam path and by means of a similar disk which is not shown but which is provided at the measurement reflector. Furthermore, the 70% calibration point is determined during the control cycle after pivoting the reference cell 43 into the beam path.

The optical head which is enclosed in the housing 22 and the measurement reflector 40 at the end of the measurement path 52 are provided with the usual flushing air adaptors.

During the measurement the basic DC current is also detected, i.e. a differential measurement takes place between the DC current pulses and the basic DC current.

The invention provides for the first time a spectroanalytical gas measuring apparatus with which an insitu measurement can be continuously carried out with a highly resolved spectrum.

What is claimed is:

1. A spectroanalytical measuring apparatus for analyzing gases present over a variable length measurement path including a first path and defined by a beam passage opening and a second path end defined by a retroreflector, comprising:
   an apparatus housing including a front and a back, and defining a beam passage opening situated in said housing back, said front defining a generally front orientation for said measuring apparatus and said back defining a generally rear orientation;

a source of electromagnetic radiation for transmitting a source radiation beam whose spectrum includes the spectral regions required for the gases to be analyzed;

a condenser lens situated so said source radiation beam is transmitted therethrough;

a deflecting mirror including a deflecting mirror tilt axis, displaceable in the direction of said source radiation beam between a first position and a second position and tiltable about said deflecting mirror tilt axis;

a beam divider situated between said condenser lens and said deflecting mirror;

a replaceable objective reflector having a chosen focal length, an angle of reflection and an objective reflector tilt axis, a shorter focal length being selected when said deflecting mirror is in said first position and a longer focal length being selected when said deflecting mirror is in said second position, said objective reflector being tiltable about said objective reflector tilt axis parallel to said deflecting mirror tilt axis;

a followup mirror including a surface;

a retroreflector, spaced apart from said housing at the second end of the beam path;

a polychromator including an entry gap, for splitting the spectrum of radiation falling upon said polychromator into component spectra;

a photoreceiver apparatus for receiving said component spectra from said polychromator and for producing therefrom electrical signals associated with specific spectral wavelengths;

said source radiation beam from said source being transmitted through said condenser lens to said beam divider;

said beam divider passing at least part of said source radiation to said deflecting mirror;

said deflecting mirror being tilted about said deflecting mirror tilt axis to deflect source radiation to said objective reflector and said deflecting mirror when ih said first position deflecting said source radiation in front of said followup mirror to said objective reflector and said deflecting mirror when in said second position deflecting said source radiation behind said followup mirror to said objective reflector;

said objective reflector being displaceable in the direction of said source radiation from said deflecting mirror and reflecting said source radiation from said deflecting mirror to said followup mirror which deflects said source radiation through said beam passage opening and said measurement path onto said retroreflector, forming thereon an image of said condenser lens; and said retroreflector further reflecting said radiation from said followup mirror back past said measurement path to said followup mirror;

said followup mirror reflecting said reflected radiation back to said objective reflector;

said objective reflector reflecting said reflected radiation back to said deflecting mirror;

said deflecting mirror tilt axis being perpendicular to a plane defined by said source radiation and said reflected radiation at said deflecting mirror, said reflected radiation being reflected from said deflecting mirror back to said beam divider which reflects at least part of said reflected radiation to said polychromator, such that a range of meaurement path lengths are accommodated by changing the position of said deflecting mirror and by replacing said objective reflector, the signals form said photoreceiver apparatus determining from the spectra from said polychromator the presence and/or quantity of gases in the measurement path.

2. The apparatus of claim 1, wherein said source of electromagnetic radiation emits ultraviolet light.

3. The apparatus of claim 1, wherein said source of electromagnetic radiation is a deuterium lamp, and wherein said source and said condenser lens are combined to form a single pre-adjusted unit.

4. The apparatus of claim 1, wherein said objective relector is a concave mirror.

5. The apparatus of claim 1, wherein said objective reflector has a shorter focal length in the range of approximately 31 cm to 40 cm, and has a longer focal length in the range of approximately 50 cm to 61 cm.

6. The apparatus of claim 1, wherein said retroreflector is a single triple mirror.

7. The apparatus of claim 6, wherein said retroreflector includes a lens having a focal length of half the distance between said retroreflector and said beam passage opening.

8. The apparatus of claim 1, wherein said beam divider is situated at a level substantially that of said beam passage opening, and wherein said deflecting mirror is located in said first position directly to the rear of said beam divider.

9. The apparatus of claim 1, wherein said source radiation beam extending from said source to said deflecting mirror subtends an angle of about 20 degrees to 40 degrees relative to a radiation beam passing centrally through said beam passage opening.

10. The apparatus of claim 1, wherein said housing proximate said deflecting mirror subtends an angle of about 20 degrees to 40 degrees relative to a radiation beam passing centrally through said beam passage opening.

11. The apparatus of claim 1, wherein said deflecting mirror is located in said first position at a level slightly higher than said followup mirror.

12. The apparatus of claim 1, wherein said deflecting mirror is located in said second position between said followup mirror and said beam passage opening, at a level higher than said followup mirror.

13. The apparatus of claim 1, further including a deflecting mirror holder, for holding said deflecting mirror, capable of being fixed in said first position and said second position on said housing, said deflecting mirror being pivotably movable in said deflecting mirror holder about said deflecting mirror tilt axis.

14. The apparatus of claim 1, further including an objective reflector holder for holding said objective reflector, said objective reflector and said objective reflector holder situated beneath said followup mirror to minimize said angle of reflection at said objective reflector.

15. The apparatus of claim 14, wherein said angle of reflection of said objective reflector is about 5 degrees to 7 degrres.

16. The apparatus of claim 1, further including an outer holding device for mounting said followup mirror, said holding device and said followup mirror mounted on said housing displaceably in the direction of said beam passage opening.

17. The apparatus of claim 16, wherein said outer holding device is mounted in said housing in a chosen one of two positions which are rotated through 180 degrees about a vertical axis relative to one another.

18. The apparatus of claim 16, wherein said followup mirror and said outer holding device are pivotable about first and second mutually perpendicular positioning axes, and further including a control motor for pivoting said folloup mirror and said outer holding device.

19. The apparatus of claim 18, wherein said first positioning axis is parallel to said deflecting mirror tilt axis, and said second positioning axis is parallel to said surface of said followup mirror.

20. The apparatus of claim 1, wherein said beam divider reflects the reflected radiation to said polychromator substantially parallel to the radiation reflected by said deflecting mirror in said first position.

21. The apparatus of claim 20, further including a receiving condenser lens, whereby said beam divider reflects radiation from said deflecting mirror to said receiving condenser lens which forms an image of said objective reflector upon said entry gap of said polychromator.

22. The apparatus of claim 21, wherein said source of electromagnetic radiation includes an emitter of visible light, and further including a visible light detector, a receiving condenser lens situated to receive radiation from said beam divider and forming an image of said objective reflector on said entry gap of said polychromator, and further including an inclined beam deflecting plate, demirrored for said transmitted radiation but reflecting for visible light, said plate situated in the path of the reflected radiation after said beam divider for deflecting visible light to said visible light detector for measuring the dust content in the beam path.

23. The apparatus of claim 22, wherein said inclined demirrored beam deflecting plate is a quartz glass plate.

24. The apparatus of claim 22, wherein said inclined beam deflecting plate is situated in front of said receiving condenser lens.

25. The apparatus of claim 22, wherein said plate deflects visible radiation perpendicular to the plane of the radiation beam.

26. The apparatus of claim 1, wherein said polychromator includes a grating for refracting the radiation from said beam divider onto a common plane with all other radiation beams, and wherein said photoreceiver apparatus comprises a plurality of photoreceivers disposed at angles of diffraction at substantially the same distance from said grating as said entry gap.

27. The apparatus of claim 1, further including a control circuit and an inclined demirrored beam divider plate, said plate situated in a path of said source radiation in front of said followup miror, for deflecting said received radiation to a four-quadrant photoelement for steering said followup mirror with said control circuit so radiation beams from said followup mirror fall centrally onto said retroreflector.

28. The apparatus of claim 27, wherein said inclined demirrored beam divider plate is a quartz glass plate.

29. The apparatus of claim 28, wherein said quartz glass plate is situated between said beam divider and said condenser lens.

30. The apparatus of claim 27, wherein said plate deflects perpendicular to the plane of the radiation beam.

31. The apparatus of claim 1, further including a reference cell containing a measurement gas, pivotably insertable after said beam divider into the path of said reflected radiation beam, for calibrating the apparatus.

32. The apparatus of claim 1, wherein said source of electromagnetic radiation is a deuterium lamp energized by a low basic DC current, substantially below the loading limit but permitting permanent operation, whereon individual DC pulses are superimposed at specific time intervals to briefly overload said source.

33. The apparatus of claim 32, wherein pulse trains are superimposed on said low basic DC current at times between said specific time intervals.

* * * * *